United States Patent
Villers et al.

(10) Patent No.: US 7,265,351 B2
(45) Date of Patent: Sep. 4, 2007

(54) METHOD AND APPARATUS FOR NON-CONTACT AND RAPID DETERMINATION OF LIQUID CONTENT

(75) Inventors: Pierre de Villers, Montreal (CA); Wes Jamroz, Montreal (CA); Denis Lafrance, Montreal (CA); Brian Wong, Montreal (CA)

(73) Assignee: MPB Communications Inc., Montreal, Quebec (CA)

( * ) Notice: Subject to any disclaimer, the term of this patent is extended or adjusted under 35 U.S.C. 154(b) by 304 days.

(21) Appl. No.: 10/725,035

(22) Filed: Dec. 2, 2003

(65) Prior Publication Data
US 2005/0115873 A1    Jun. 2, 2005

(51) Int. Cl.
*G01J 5/00*    (2006.01)
(52) U.S. Cl. .................................... 250/338.1
(58) Field of Classification Search .............. 250/338.1
See application file for complete search history.

(56) References Cited

U.S. PATENT DOCUMENTS

| | | |
|---|---|---|
| 3,748,473 A | 7/1973 | Chen |
| 3,851,175 A | 11/1974 | Dahlin et al. |
| 3,965,356 A | 6/1976 | Howarth |
| 4,052,615 A | 10/1977 | Cho |
| 4,266,878 A | 5/1981 | Auer |
| 4,300,049 A | 11/1981 | Sturm |
| 4,465,929 A | 8/1984 | Edgar |
| 4,577,104 A | 3/1986 | Sturm |
| 4,612,802 A | 9/1986 | Clarke et al. |
| 4,634,856 A | 1/1987 | Kirkham |
| 4,733,078 A | 3/1988 | Sturm |
| 4,755,678 A | 7/1988 | Izatt et al. |
| 4,766,319 A | 8/1988 | Regimand |
| 4,788,853 A | 12/1988 | Bell |
| 4,823,008 A | 4/1989 | Sturm |
| 4,840,706 A | 6/1989 | Campbell |
| 4,853,614 A | 8/1989 | Carver |
| 4,864,850 A | 9/1989 | Price |
| 4,879,471 A | 11/1989 | Dahlquist |
| 4,928,013 A | 5/1990 | Howarth et al. |
| 5,270,546 A | 12/1993 | Jamroz et al. |
| 5,357,112 A | 10/1994 | Steele et al. |
| 5,396,260 A * | 3/1995 | Adel et al. ................. 345/91 |
| 5,594,340 A | 1/1997 | Coyle et al. |
| 5,668,479 A | 9/1997 | Jackson et al. |
| 5,801,537 A | 9/1998 | Siddiqui et al. |
| 5,870,926 A | 2/1999 | Saito |

* cited by examiner

Primary Examiner—David Porta
Assistant Examiner—Mark R. Gaworecki
(74) Attorney, Agent, or Firm—Bereskin & Parr (57) ABSTRACT

A method and apparatus for non-contact determination of liquid concentrations such as the content of water, oil, dye, paint, fuel, glue, etc., in a moving or stationary mass of production such as wood, paper, powders, fabrics, sand, bricks, concrete, plants, and the like, or in other liquids such as oil spills in water, is provided. The method comprises measuring the passive emissivity of a substance, using an imaging radiometer. It has been found that an emissivity image may be used to quantify the liquid content in a substance. The invented method allows for non-contact, rapid and continuous in-line measurements.

9 Claims, 6 Drawing Sheets

METHOD AND APPARATUS FOR NON-CONTACT AND RAPID DETERMINATION OF LIQUID CONTENT

FIELD OF THE INVENTION

The present invention generally relates to determination of liquid concentrations, and particularly to a method and apparatus for non-contact and rapid determination of a liquid content in a moving or stationary mass of products or in other liquids.

BACKGROUND OF THE INVENTION

In today's industries there are frequent needs for in-line measurements of a liquid concentration within a substance, such as the content of water, oil, dye, paint, fuel, glue, etc. within materials such as wood pieces, logs, lumber, veneer, paper, powders, cardboard, fabrics, sand, soil, plants, bricks, concrete and the like; or within other liquids such as in the case of oil spills in water. The conventional method of liquid content measurement, such as a content of water, is based on the difference between the weight of the substance before and after heating it at a temperature close to or above the boiling point of the particular liquid. However, such a method requires long periods of time which may be as much as twenty-four hours or longer, and is limited mostly to the measurement of stationary substances. Therefore this conventional method is not practical for in-line applications where virtually instantaneous measurements are required.

Another method of liquid content determination which is popularly used in the industry, is based on spectral selective optical absorption which can be measured in scattered and/or transmitted light beams. Sets of light sources with precisely selected wavelengths are used in this method. One set of wavelengths which is relatively unaffected by the characteristic being measured, is used as a reference. The other set of wavelengths is tuned to the liquid absorption peak level. Several versions of this approach have been disclosed, in which conventional infrared optical sources are applied, as for example described in U.S. Pat. No. 4,266,878, issued to Auer on May 12, 1981; U.S. Pat. No. 4,634,856, issued to Kirkham on Jan. 6, 1987; U.S. Pat. No. 4,788,853, issued to Bell on Dec. 6, 1988; U.S. Pat. No. 3,851,175, issued to Dahlin et al. on Nov. 26, 1974; U.S. Pat. No. 3,965,356, issued to Howarth on Jun. 22, 1976; U.S. Pat. No. 4,052,615, issued to Cho on Oct. 4, 1977; U.S. Pat. No. 4,300,049, issued to Sturm on Nov. 10, 1981; U.S. Pat. No. 4,465,929, issued to Edgar on Aug. 14, 1984; U.S. Pat. No. 4,577,104, issued to Sturm on Mar. 18, 1986; U.S. Pat. No. 4,733,078, issued to Sturm on Mar. 22, 1988; U.S. Pat. No. 4,823,008, issued to Sturm on Apr. 18, 1989; U.S. Pat. No. 4,840,706, issued to Campbell on Jun. 20, 1989; U.S. Pat. No. 4,879,471, issued to Dahlquist on Nov. 7, 1989; U.S. Pat. No. 4,928,013, issued to Howarth et al. on May 22, 1990; and U.S. Pat. No. 5,870,926, issued to Saito on Feb. 16, 1999. It is also known that a sub-millimeter laser instead of the conventional infrared optical sources can be used in this method, as disclosed in U.S. Pat. No. 4,755,678, issued to Izatt et al. on Jul. 5, 1988. The applications disclosed in these prior art patents generally apply to moisture measurements either in soil or paper products.

It is also known in the industry that moisture measurements can be based on absorption of fast neutron rays gamma radiation, examples of which are disclosed in U.S. Pat. No. 4,766,319, issued to Regimand on Aug. 23, 1988 and U.S. Pat. No. 3,748,473, issued to Chen on Jul. 24, 1973.

In-line moisture measurements can also be conducted by using NMR sensors. Apparatus for in-line moisture measurements based on a NMR sensor is disclosed in U.S. Pat. No. 5,594,340, issued to Coyle et al. on Jan. 14, 1997.

Meters for measuring electrical properties of a substance are used for liquid content measurements where a relationship between the electrical properties and the liquid of the substance can be established. For example, the moisture content of a substance may be estimated from electrical properties such as resistance, capacitance and conductivity. However, these types of meters are limited to the lower end of the liquid content. The moisture content range which can be measured by the electrical meters is from 6 percent to 27 percent according to The Standard Test Methods (ASTM: D 4444-84). Therefore, the meters cannot be used efficiently outside of the above mentioned moisture content range because high moisture levels cause no substantial change in electrical properties. Examples of moisture measurements based on electrical properties of a material are disclosed in U.S. Pat. No. 4,853,614, issued to Carver on Aug. 1, 1989; U.S. Pat. No. 4,864,850, issued to Price on Sep. 12, 1989; U.S. Pat. No. 5,668,479, issued to Jackson et al. on Sep. 16, 1997; and U.S. Pat. No. 5,801,537, issued to Siddiqui et al. on Sep. 1, 1998.

It is also well known in the industry to uniformly heat a substance and then to monitor temperature of the heated substance for determination of the moisture content or identification of defects in the substance. U.S. Pat. No. 4,612,802, issued to Clarke et al. on Sep. 23, 1986 discloses a method of non-contact moisture measurements in which an area of one surface of a substance is subjected to a predetermined intensity of heat for a selected period of time. The moisture content is determined by measuring the temperature rise of the heated surface of the substance. U.S. Pat. No. 5,357,112, issued to Steele et al. on Oct. 18, 1984 discloses a method of uniformly heating wood and then submitting the wood to an infrared camera to provide a thermal image of the surface of the wood. The thermal images of the preheated wood are used for identification of knots and/or voids in lumber surfaces. These methods for determination of moisture content require uniform heating of the substance to be measured, which may not be practically applicable under some circumstances. Therefore the application thereof is limited.

U.S. Pat. No. 5,270,546, issued to Jamroz et al. on Dec. 14, 1993 discloses a method and apparatus for non-contact moisture measurements based on infrared radiation absorbed by water present within a substance. In this method the surplus of infrared radiation causes modifications of a substance's surface by changing its microstructure. The density of surface modifications relates to the moisture content of the substance, and an analysis of a portion of the substance's surface can accurately approximate the average moisture content of the substance.

Nevertheless, there is still a need for improved methods and apparatus for non-contact and rapid moisture measurements which can be conveniently used in various applications, particularly in a passive manner without the need to apply infrared radiation or heating.

SUMMARY OF THE INVENTION

One object of the present invention is to provide a method for non-contact and rapid determination of a liquid content of a substance.

Another object of the present invention is to provide a method for sorting wood and kiln drying same, based on data representing two-dimensional moisture distribution in a plurality of pieces of wood.

A further object of the present invention is to provide a method for non-contact determination of a structural inhomogeneity of a sample of a substance.

A still further object of the present invention is to provide an apparatus for non-contact measurements of liquid content of a substance in a passive manner.

In accordance with one aspect of the present invention, there is a method provided for non-contact determination of a liquid content of a sample of a substance. The method comprises exposing the sample to an environment in which said liquid evaporates from the surface of the sample, resulting in a temperature change; obtaining a emissivity image of the sample; and processing the image to determine the liquid content of the substance.

The processing preferably determines a spatial distribution of the liquid content over at least a portion of the surface of the sample.

In accordance with another aspect of the present invention, there is a method provided for non-contact determination of structural inhomogeneity of a sample of a substance. The method comprises exposing the sample to an environment in which a liquid evaporates from a surface of the sample, resulting in a temperature change; obtaining an emissivity image of the sample of the substance; converting the obtained emissivity image into digital data; processing the data using gray level calibration curves to measure variation in a two-dimensional liquid distribution of the substance; and determining the structural inhomogeneity of the sample of the substance in accordance with the measured variation in the two-dimensional liquid distribution of the substance.

One of the gray level calibration curves is preferably generated from a plurality of measured gray level values of an emissivity image of a reference sample of the substance, with a known liquid content of the liquid within a selected range of ambient temperature and relative humidity.

In accordance with a further aspect of the present invention, there is a method provided for sorting wood and kiln drying same. The method comprises steps of obtaining a set of data representing two-dimensional moisture distribution in a plurality of pieces of wood; in accordance with the data of two-dimensional liquid distribution in the respective pieces of wood, sorting the pieces of wood into batches having similar drying characteristics according to said two-dimensional liquid distribution therein; and drying the batches in a kiln drier according to drying program determined for each individual batch.

The drying program preferably comprises the temperature and duration of kiln drying. The temperature and duration of said kiln drying depend on an evaluation of said drying characteristics.

In accordance with a still further aspect of the present invention there is an apparatus for non-contact measurements of a liquid content of a substance. The apparatus comprises a radiometer for recording an emissivity image of the substance. The apparatus further includes means for storing the emissivity image of the substance, means for recording an ambient temperature, and means for recording a relative humidity. There are further provided to the apparatus, means for converting the emissivity image into digital data, and a computing device for data processing and for determining the liquid content of the substance.

The apparatus preferably includes means for generating gray level calibration curves for use in the data processing and for determining the liquid content of the substance. It is also preferable that the apparatus further includes a database of a plurality of sets of gray level values corresponding to a plurality of emissivity images of reference samples of substances with known liquid contents at a selected range of ambient temperature and relative humidity.

The method and apparatus of the present invention allows for non-contact and rapid measurements of the liquid content of a stationary substance as well as a fast moving substance. The method and apparatus of the present invention also allow for the determination of the presence of liquid within a substance, such as water trapped by degenerated cells in wood. In addition, the method and the apparatus of the present invention allow for the determination of structural inhomogeneities within a substance by measuring the variation in the liquid content distribution within the substance.

The present invention advantageously provides means for measurements over the entire surface of a sample and over the entire range of the liquid content. The method of the present invention is advantageously based on passive measurements and therefore neither external illumination nor heating is required. The measurements may be instantly carried out by infrared imaging radiometers so that the apparatus can be placed at a distance from the substance being analyzed. All these advantages make the present invention useful in various applications. For example, a method for sorting wood and kiln drying same can be adapted to allow grouping of batches of the wood based on two-dimensional moisture distribution so that a corresponding kiln drying program can be determined for each individual batch of wood and conducted for a faster drying result while preventing the wood from being overdried.

Other features and advantages of the present invention will be better understood with reference to the preferred embodiments described hereinafter.

BRIEF DESCRIPTION OF THE DRAWINGS

Having thus generally described the nature of the present invention, reference will now be made to the accompanying drawings, showing by way of illustration the embodiments thereof, in which.

DETAILED DESCRIPTION OF THE PREFERRED EMBODIMENTS

The method for non-contact and rapid measurements of a liquid content of a substance is based on the principle that the substance emissivity depends on the amount of liquid in that substance. Furthermore, it has been determined that an empirical model exists which describes the quantitative relationship between the substance emissivity and the liquid contents in that substance. The substance emissivity is measurable. Therefore, the liquid content in that substance can be measured and analyzed through recording of the emissivity of the substance.

The liquid content of a substance, which is not in equilibrium with the ambient relative humidity, will be changing by way of liquid evaporation. The flux of this evaporation is proportional to the liquid content. According to Fick's first law, the flux of liquid evaporation may be expressed in the following way:

$$\Phi = -D\frac{\Delta C}{\Delta x} = \frac{A}{\Delta x}(M_{sub} - M_{eq}) \qquad [1]$$

$\Phi$ — the flux of the evaporation $\left[\frac{kg}{m^2 sec}\right]$ $D$ — diffusion coefficient for vapor $\Delta C$ — the liquid concentration gradient over a distance $\Delta x$ $\Delta x$ — boundary layer thickness $A$ — constant $M_{sub}$ — the liquid content (the amount of liquid contained in a substance, usually expressed as a percentage of the mass of the dry substance)

$M_{eq}$ — the equilibrium liquid content (i.e. a liquid content at which a substance neither gains nor loses liquid to the surrounding air)

The energy loss due to the evaporation process affects the emissivity ($E_{sub}$) of a substance. Therefore, the equation [1] indicates that there is a relationship between the liquid content and the emissivity of a substance. This relationship may be expressed as:

$$E_{sub} = \psi(M_{sub} - M_{eq}) \qquad [2]$$

where:

$E_{sub}$ — the emissivity of a substance

The function $\psi$ can be determined empirically for a given substance by measuring the substance emissivity ($E_{sub}$) as a function of the liquid content ($M_{sub}$). The liquid content equilibrium ($M_{eq}$) for a given substance can be determined for a selected range of relative humidity ($H_{rel}$) and ambient temperature T, either by a direct measurement of a reference sample or by calculations.

For example, in the case of the moisture content in solid wood, the empirical relationship between the equilibrium moisture content ($M_{eq}$) and the ambient relative humidity ($H_{rel}$) can be approximated using the following equation:

$$M_{eq} = \frac{a}{W}\left[\frac{KH_{rel}}{1-KH_{rel}} + \frac{K_1KH_{rel} + 2K_1K_2K^2H_{rel}^2}{1+K_1KH_{rel}+K_1K_2K^2H_{rel}^2}\right] \qquad [3]$$

where:

$M_{eq}$ — the equilibrium moisture content [%];

a — constant (=1800);

$H_{rel}$ — relative humidity [fractional];

W, K, $K_1$, and $K_2$ — temperature (T) dependent parameters;

T — temperature (° C.)

The temperature dependent parameters are determined by the following equations:

$W = 349 + 1.29\ T + 0.0134\ T^2$ $K = 0.805 + 0.000736\ T - 0.00000273 T^2$ $K_1 = 6.27 - 0.00938\ T - 0.000303 T^2$ $K_2 = 1.91 + 0.0407\ T - 0.000293\ T^2$

Thus, the liquid content of a substance can be determined by using equation [2] and measurements of the emissivity of a substance ($E_{sub}$).

Figure 1:
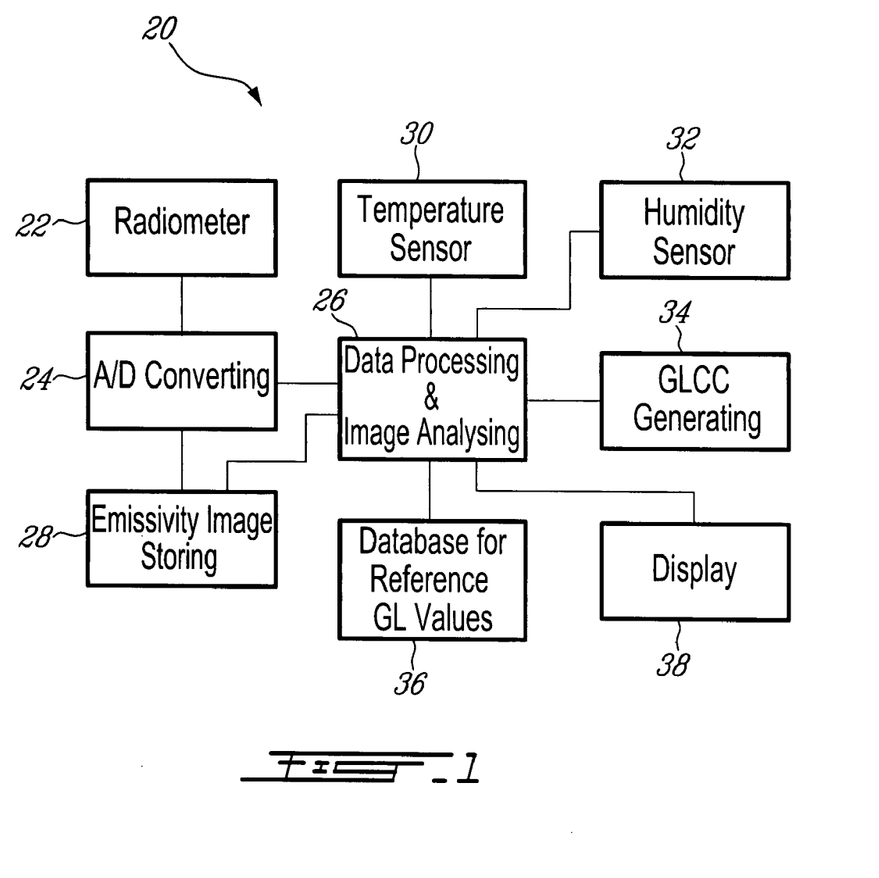
FIG. 1 is a diagram illustrating functional features of a system of the present invention for non-contact determination of a liquid content of a sample of a substance.

Referring to FIG. 1, the method for non-contact and rapid measurements of the liquid content of a substance according to the present invention is implemented by a system generally indicated at numeral 20, which includes an imaging radiometer 22. In order to measure the emissivity of a liquid content of a substance, the substance must be positioned in an environment in which the liquid evaporates from the surface of the substance, resulting in temperature changes on the surface of the substance. The imaging radiometer 22 generally includes either cooled or un-cooled microbolometer infrared focal plane array detectors, and is therefore adapted for detecting the temperature changes of individual points within an effective area of the surface of the substance, and for generating a plurality of signals representing an emissivity image of the detected area of the surface of the substance.

These image signals are converted by an A/D converter 24 into digital signals which are then sent to a data processor 26 and/or a memory unit 28. The digital image signals are processed by the data processor 26 and therefore, the emissivity of the substance ($E_{sub}$) of the equation [2] is obtained.

The equilibrium liquid content ($M_{eq}$) of equation [2] can be determined by using equation [3] in which ambient temperature and relative humidity must be measured and input thereinto. The system 20 therefore includes a temperature sensor 30 and a relative humidity sensor 32 for measuring the ambient temperature and the relative humidity, the readings of which are put into the data processor 26. Thus, the ($M_{eq}$) of equation [2] is obtained.

In order to calculate the liquid content ($M_{sub}$) when the emissivity value ($E_{sub}$) and the liquid content equilibrium ($M_{eq}$) in equation [2] are known, the function $\Psi$ must be established. The function $\Psi$ can be empirically established by measuring the image gray level value of the emissivity image of a known liquid content of a given reference liquid at a given temperature and a given relative humidity. When the known liquid content changes, a plurality of image gray level values can be obtained, and thereby a gray level calibration curve for this reference substance can be generated. When the given temperature and the relative humidity change respectively within a predetermined range, a set of gray level calibration curves for this given reference substance is generated. Similarly, a plurality of sets of gray level calibration curves can be generated for a selected group of reference substances within the predetermined temperature and relative humidity ranges. This operation is illustrated by block 34. The generated gray level calibration curve data is stored in database 36.

Therefore, the function $\Psi$ in equation [2] is established in the form of a plurality of sets of gray level calibration curves, and the data processor 26 is enabled to retrieve the relevant reference gray level calibration curve data to analyze the emissivity image data, thereby generating liquid content information relating to the individual points of the surface of the substance being measured. This liquid content information can be displayed in a two-dimensional image, as illustrated by block 38.

Figure 2:
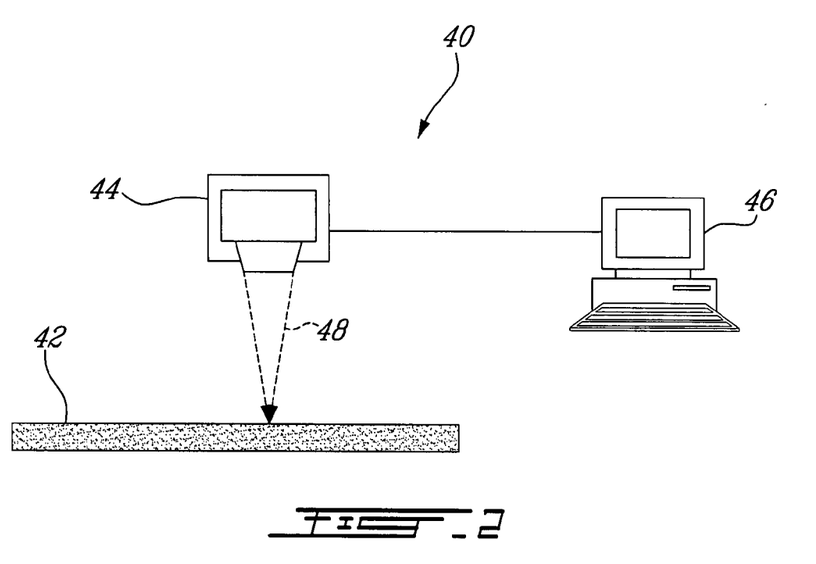
FIG. 2 is a schematic view of an apparatus according to one embodiment of the present invention, showing a single imaging radiometer being used for recording an emissivity image of one side of a substance.

In FIG. 2, an apparatus 40 according to one embodiment of the present invention is suitable for liquid content measurements in a stationary sample 42 of a substance. Apparatus 40 includes an imaging radiometer unit 44 connected to a computer unit 46. The imaging radiometer unit 44 includes cooled or un-cooled microbolometer infrared focal plane array detectors, hybrid optics, an embedded processor and a digital processing/storage system. Thus, the imaging radiometer unit 44 performs the combined functions of blocks 22, 24, 28 of the system 20 shown in FIG. 1. The passive emission from the sample 42 is represented by arrow 48. The computer unit 46 is equipped with a frame grabber for recording the emissivity images, and with an image analyzer for generating the gray level calibration curve. The computer unit 46 is also equipped with a database of referenced gray level calibration curve data. Therefore, the computer unit 46 performs the combined functions illustrated by blocks 26, 34, 36 and 38 of the system 20 of FIG. 1.

The temperature sensor 30 and the relative humidity sensor 32 of the system 20 shown in FIG. 1 can be incorporated into the imaging radiometer unit 44 and generate the temperature and humidity signals which are sent to the computer unit 46. Alternatively, temperature and relative humidity readings obtained from temperature and humidity meters which are separated from the apparatus 40, may be manually input into the computer unit 46.

The imaging radiometer unit 44 is positioned at one side of the sample 42 and the liquid content measurements are based on passive emissions from a surface of one side of the sample 42.

Figure 3:
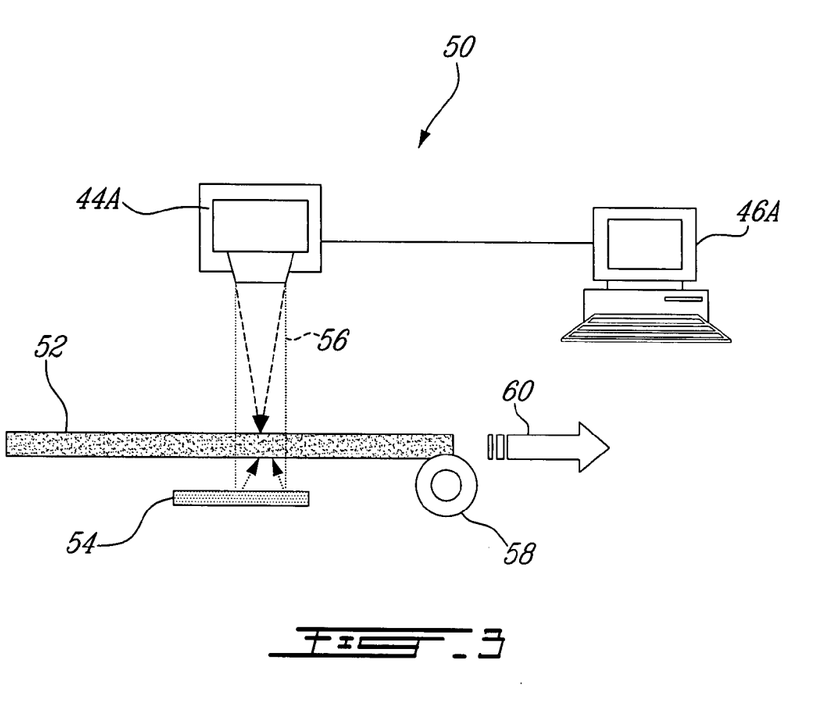
FIG. 3 is a schematic view of the apparatus according to another embodiment of the present invention, showing a single imaging radiometer and a reflective mirror for simultaneously recording an emissivity images of two sides of a substance.

In FIG. 3, an apparatus 50 according to another embodiment of the present invention is used in situations where liquid content measurements are taken on a moving sample 52. Apparatus 50 includes an imaging radiometer unit 44A which is similar to the imaging radiometer unit 44 of FIG. 2 and is additionally equipped with an optical encoder to monitor the speed of the moving sample 52. The passive emission from both sides of the sample 52 is represented by arrows 56. A reflector 54 is positioned at a side of the moving sample 52 opposite to the side where the imaging radiometer unit 44A is positioned. Thus, data on emissivity images from both sides of the sample 52 is collected and processed by the single radiometer unit 44A. More than one reflector 54 may be needed depending on the size and shape of the moving sample 52.

Apparatus 50 further includes the computer unit 46A which is similar to the computer unit 46 of FIG. 2, and will not therefore be further described.

The moving sample 52 is positioned on a plurality of rollers 58 (only one shown) and is moved in a direction as indicated by arrow 60. The moving sample 52 however, can be positioned on and moved by other types of devices which will not be discussed herein because the moving devices are not part of the present invention and are known in the prior art.

It should be understood that apparatus 50 is also suitable for measuring the liquid content of a stationary sample, such as the sample 42 of FIG. 1.

Figure 4:
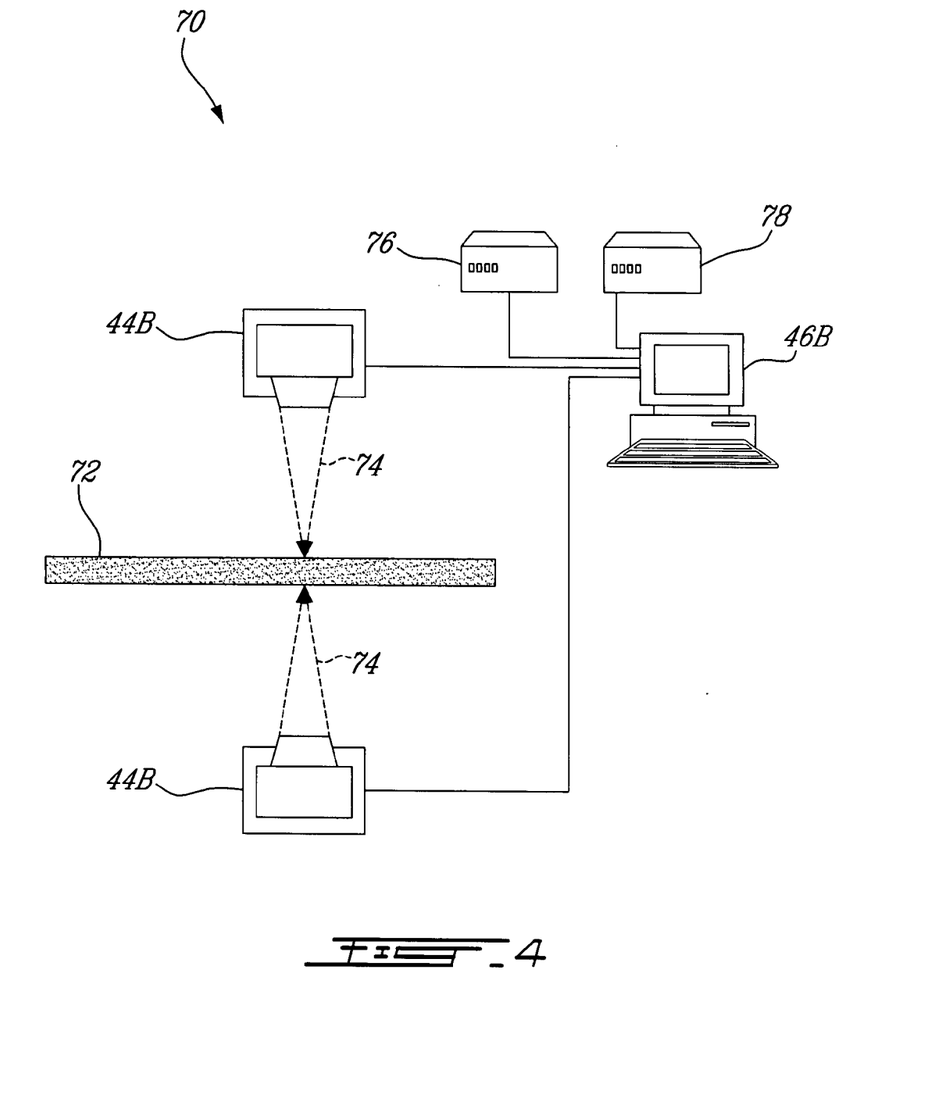
FIG. 4 is a schematic view of the apparatus according to a further embodiment of the present invention, showing two imaging radiometers for simultaneously recording emissivity images of two sides of a substance.

In FIG. 4, apparatus 70 according to a further embodiment of the present invention includes two imaging radiometer units 44B, similar to the imaging radiometer unit 44 of FIG. 2 and will not therefore be further described. The passive emissions from both sides of a sample 72 are represented by arrows 74. The respective radiometer units 44B are positioned at opposed sides of the sample 72. Apparatus 70 further includes a computer unit 46B which is similar to the computer unit 46 of FIG. 2 and will therefore not be further described. The apparatus 70 is equipped with a temperature measuring device 76 and a humidity measuring device 78 to generate signals corresponding to the ambient temperature and the relative humidity. The temperature measuring device 76 and the humidity measuring device 78 are directly connected to the computer unit 46B such that the generated signals are transmitted to the computer unit 46B for data processing.

It should be understood that the method and apparatus of the present invention can be broadly used for in-line measurements of liquid concentrations such as a content of water, oil, dye, paint, fuel, glue, and the like, in materials such as wood pieces, logs, lumber, veneer, paper, powders, cardboard, fabrics, sand, soil, plants, bricks, concrete, and the like, or in liquids, such as oil spills in water.

It should be further understood that the method and apparatus of the present invention can also be used for determination of the structural inhomogeneity of a sample of a substance. People skilled in the art will understand that the structural inhomogeneity of a sample of a substance can be similarly determined according to the present invention by measuring the variation in two-dimensional liquid distribution of the substance.

In a still further embodiment of the present invention, the method and apparatus for non-contact and rapid measurements of the liquid content of a sample of a substance can be applied for sorting wood and kiln drying same in a wood processing program. A number of pieces of wood to be dried are processed with the apparatus of the present invention, and data representing two-dimensional moisture distribution in each piece of wood is obtained. The pieces of wood are then sorted into batches having similar drying program needs according to the two-dimensional moisture distribution therein. Each drying program generally includes the temperature and duration of the drying. The temperature and duration of the drying phase depend on an evaluation of a water content within the two-dimensional moisture distribution.

The temperatures and durations of the drying phase varies in different drying programs to meet the assessed needs of the wood within each batch. Thus, the pieces of wood can be rapidly and efficiently dried without the risk of being over-dried.

In the following examples an imaging radiometer (FLIR SYSTEMS model Thermovision MV®) has been used as the monitor of infrared emissions. The distance between the sample surface and the radiometer was approximately between 1 and 12 feet. The computer was equipped with a frame grabber (Matrox®).

EXAMPLE 1

Figure 5:
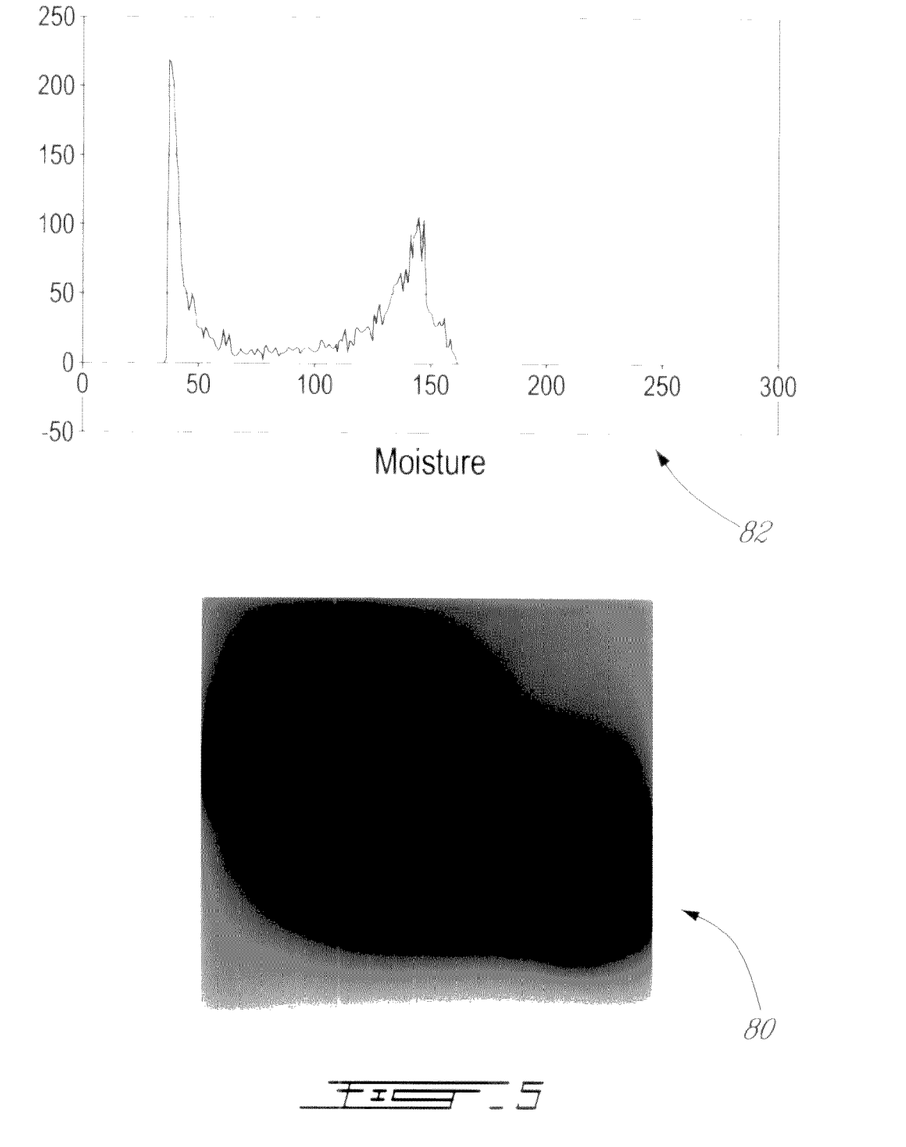
FIG. 5 is an illustration presenting an emissivity image and a moisture content distribution in a stationary sample of paper obtained using the method of the present invention.

A piece of 8 by 8 inch paper was analyzed with the described apparatus. The sample was stationary. An emissivity image 80 of the sample recorded by the imaging radiometer, and the corresponding moisture content histogram 82, are shown in FIG. 5. The vertical axis illustrates the number of pixels. The horizontal axis of the histogram 82 was calibrated as a percentage of the moisture content. The peak on the left side of the histogram 82 corresponds to the dry paper, i.e. paper that is in equilibrium with the surroundings at the given relative humidity and the ambient temperature. This peak is used as a reference point for system calibrations. The wide curve on the right side of the reference peak illustrates the water content and its distribution over the analyzed area of the sample.

EXAMPLE 2

Figure 6:
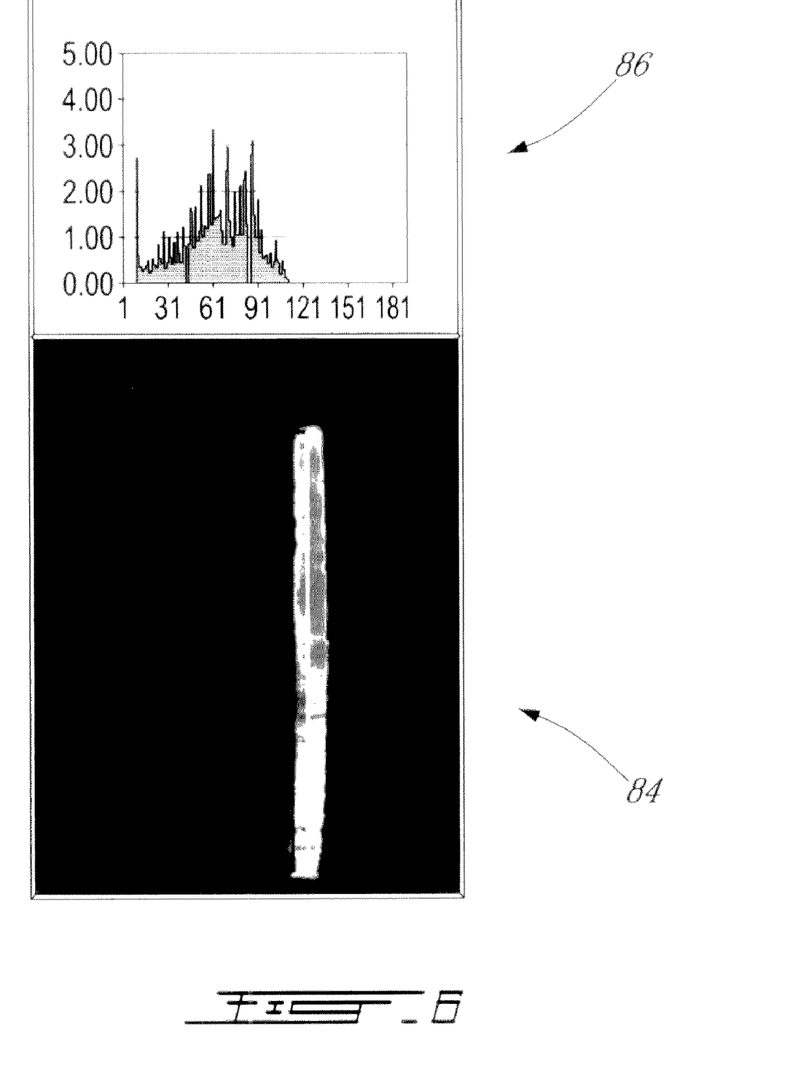
FIG. 6 is an illustration presenting an emissivity image and a moisture content distribution in a moving sample of solid wood obtained using the method of the present invention.

A piece of 2 by 4 inch pine board was analyzed by the described apparatus. During the analysis process the sample was moving at a speed of 250 feet/minute. An emissivity image 84 of the sample which was recorded with the imaging radiometer, and the measured moisture content histogram 86 for the sample are shown in FIG. 6.

EXAMPLE 3

Figure 7:
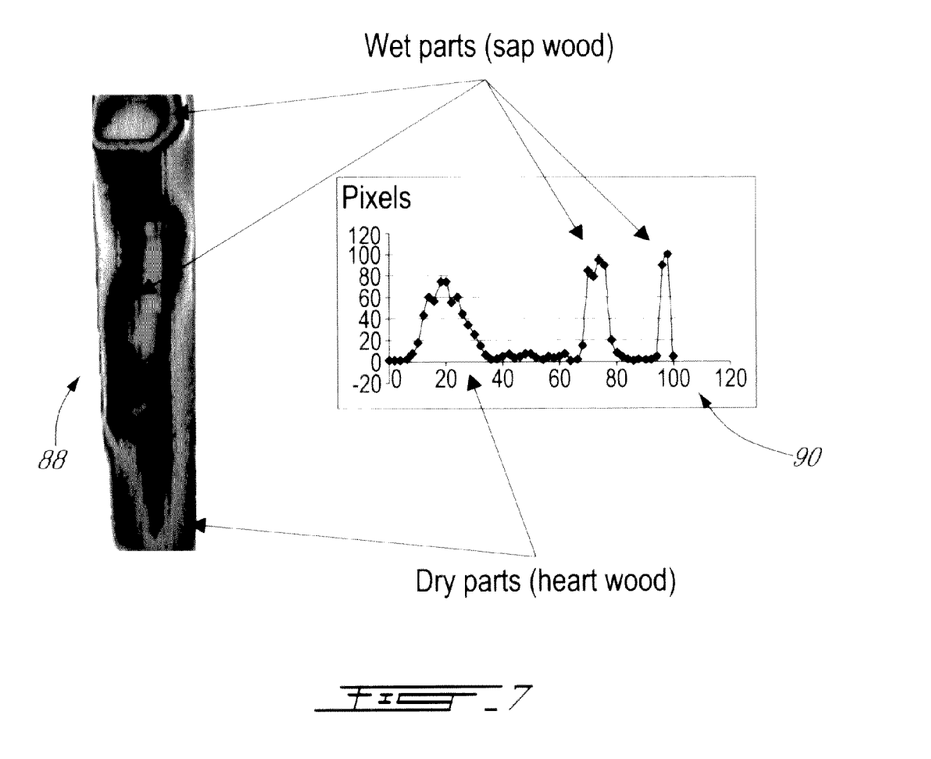
FIG. 7 is an illustration presenting an emissivity image and a corresponding gray level calibration curve of a mixed sap and heart wood board.

The structural inhomogeneity of a wooden board that contained a mix of sap wood and heart wood was analyzed with the described apparatus. A typical result of the water content distribution that is related to the presence of structural inhomogeneity is illustrated in FIG. 7, in which the emissivity image 88 is generated by an imaging radiometer, and the histogram 90 represents a corresponding grey level calibration curve.

Modifications and improvements to the above-described embodiments of the present invention may become apparent to those skilled in the art. The foregoing description is intended to be exemplary rather than limiting. The scope of the present invention is therefore intended to be limited solely by the scope of the appended claims.

We claim:

1. A method for non-contact determination of structural inhomogeneity of a structure, comprising:
   obtaining an emissivity image of the structure;
   using gray level calibration curves to measure variation in a two-dimensional distribution within said image to determine the structural inhomogeneity of the structure.

2. A method as claimed in claim 1, wherein said structure is exposed to an environment in which a liquid evaporates from a surface of the structure, resulting in a temperature change on the surface, said using gray level calibration curves comprises generating one of the gray level calibration curves from a plurality of measured gray level values of an emissivity image of a reference structure with a known liquid content of the liquid within a selected range of ambient temperatures and relative humidity, said determining comprises determining an ambient relative humidity of the environment, said structural inhomogeneity being liquid content dependent.

3. A method as claimed in claim 2 comprising recording the emissivity image of both the structure to be measured and the reference structure using an imaging radiometer.

4. A method for sorting wood and kiln drying same comprising: determining a two-dimensional moisture content distribution of a plurality of pieces of wood according to claim 2 and wherein moisture evaporates from a surface of the wood, resulting in a temperature change on the surface;
   sorting the pieces of wood into batches having similar drying program needs according to said two-dimensional moisture distribution therein; and
   drying the batches in a kiln drier according to said drying program determined for each individual batch.

5. A method as claimed in claim 4, wherein said drying program comprises a temperature and duration of drying depending on an evaluation of the liquid content within said two-dimensional moisture distribution.

6. A method as claimed in claim 1 wherein the emissivity image of the structure to be measured is obtained from one side of the structure.

7. A method as claimed in claim 1 wherein the emissivity image of the structure to be measured is obtained from opposed sides of the structure.

8. A method as claimed in claim 7 wherein the emissivity image of the structure to be measured is recorded from opposed sides of the structure using a single imaging radiometer.

9. A method as claimed in claim 7 wherein the emissivity image of the structure to be measured is recorded from opposed sides of the sample of the structure using a pair of imaging radiometers positioned at the opposed sides of the structure.

* * * * *